United States Patent [19]

Bohn et al.

[11] 4,367,115

[45] Jan. 4, 1983

[54] DEVICE FOR CONTROLLING A PANEL PRESS FOR THE ASSEMBLY OF MULTILAYER PRINTED CIRCUIT BOARDS

[75] Inventors: Hans Bohn, Schopfloch; Wolfgang Stein, Freudenstadt; Peter Bernsau, Wittlensweiler; Fred Staubitzer, Dornstetten, all of Fed. Rep. of Germany

[73] Assignee: Robert Bürkle GmbH & Co., Freudenstadt, Fed. Rep. of Germany

[21] Appl. No.: 310,929

[22] Filed: Oct. 13, 1981

[30] Foreign Application Priority Data

Oct. 10, 1980 [DE] Fed. Rep. of Germany ....... 3038288

[51] Int. Cl.³ ........................................... G05G 15/00
[52] U.S. Cl. ..................................... 156/358; 100/51
[58] Field of Search .................. 156/358, 359; 100/48, 100/50, 51, 93 P

[56] References Cited

U.S. PATENT DOCUMENTS

| 3,925,139 | 12/1975 | Simmons | 156/358 |
| 3,935,053 | 1/1976 | Armstrong | 156/358 X |
| 3,979,248 | 9/1976 | Kussmaul | 156/358 |
| 4,264,394 | 4/1981 | Izumihava | 156/358 |

*Primary Examiner*—David A. Simmons
*Attorney, Agent, or Firm*—Joseph A. Geiger

[57] ABSTRACT

A device for controlling a heated panel press in the switchover from a contact pressure mode to a curing pressure mode, in connection with the assembly of multilayer stacks of printed circuit boards with interposed thermosetting resinous bonding layers, the device consisting essentially of a displacement transducer measuring the decrease in the stack height in terms of displacement pulses and a pulse counter and count comparator producing a switchover signal at a predetermined threshold count which reflects attainment of the flux point in the bonding layer resin. After an adjustable delay, the switchover signal is transmitted to the control unit of the press.

4 Claims, 1 Drawing Figure

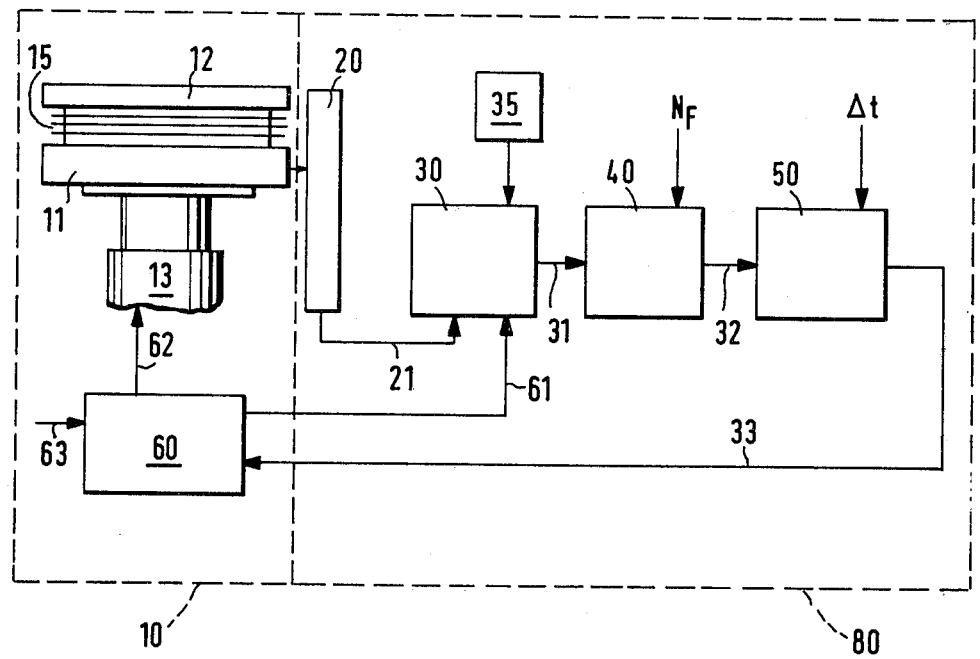

DEVICE FOR CONTROLLING A PANEL PRESS FOR THE ASSEMBLY OF MULTILAYER PRINTED CIRCUIT BOARDS

BACKGROUND OF THE INVENTION

1. Field of the Invention

The present invention relates to equipment for the production of printed circuit board and, more particularly, to a device for controlling the pressing action of a panel press with reference to the flux point of thermosetting resinous bonding layers in connection with the assembly of multilayer printed circuit boards.

2. Description of the Prior Art

The production of multilayer printed circuit boards involves the assembly of a stack of circuit boards, in alternation with resinous bonding layers and the application to the stack of controlled heat and pressure by means of a heated panel press. The latter is preferably a multi-stage press suitable for the simultaneous production of a number of multilayer printed circuit boards.

The application of controlled heat to the resinous bonding layers results in a succession of physical and chemical changes in the resin, beginning with a plastification process which reaches a flux point at which the bonding layer has a minimal viscosity and a high wetting factor for good adhesion. With increasing temperature, the resin undergoes a polycondensation process, as a result of which it gels and rapidly increases in its viscosity. The resin now undergoes a curing phase, at the end of which it is transformed into a permanently hardened, rigid state.

Different levels of pressure must be applied to the multilayer stack during this bonding layer transformation. A moderate contact pressure, or heat transfer pressure, is applied during the major part of the heat buildup phase, and a much higher curing pressure is applied in the latter part of the curing phase and during at least an initial portion of the cooling phase. The selection of the point in time at which the full curing pressure is applied to the multilayer stack is crucial for the production quality, in terms of the permanent physical characteristics obtained in the interface between the printed circuit boards and the intermediate bonding layers.

It is possible to apply the curing pressure too soon, at a point at which the viscosity of the resin in the bonding layers is still very low, i.e. at or near the "flux point", with the result that the bonding layers will be squeezed too thin and/or undesirable deformations take place in the printed circuit boards themselves. It is also possible to apply the curing pressure too late, at a point at which the gelling of the resin has progressed so far that the bonding layer is no longer susceptible to compression and flow deformation, with the result that the bond interfaces are inadequately engaged and include cavities.

Accordingly, the switchover from the contact pressure to the curing pressure should take place with a predetermined delay from the point at which the flux point has been reached. The timing of the switchover, therefore, rests on a reliable determination of the flux point during the pressing operation.

It has already been suggested that, by measuring the relative displacements between the press table and the upper press plate, it is possible to obtain a measure of the viscosity of the resin of the bonding layers, inasmuch as these layers undergo compressive deformation and the height of the multilayer stack decreases.

This suggestion is contained in a report published in the German journal "Plastverarbeiter", Volume 30 (1979), No. 9, pp. 519-23. This report suggests the connection to the press table of a friction-wheel-driven potentiometer and the comparison of the potentiometer signal with a reference signal, to obtain a compression graph of the multilayer stack and to derive from the compression graph the point at which the switchover to the curing pressure is to take place.

This method of determining the switchover point, while being satisfactory on an experimental level, is labor-intensive under production conditions, because it requires the intervention of a skilled press operator who, based on his interpretation of the compression graph produced by the displacement measuring device, has to make the decision to switch the panel press from the contact pressure level to the curing pressure level.

The prior art experimental setup also addresses itself to a source of distortion in the displacement values of the compression graph, distortions which are the result of thermal expansion of the press parts. In order to determine the extent of these distortions, the report suggests the tracing of a corrective compression graph with a set of non-compressible, fully hardened multilayers, under identical operating conditions.

SUMMARY OF THE INVENTION

Underlying the present invention is the objective of devising an improvement in the pressure control system of a heated panel press in the form of a device which makes possible the automatic switchover of the press operation from a contact pressure mode to a curing pressure mode, in response to a predetermined compression displacement of the multilayer stacks which is reflective of the attainment of the flux state.

The present invention proposes to attain this objective by suggesting a switchover control device which is adapted for use with the pressure control unit of a hydraulically driven heated panel press which includes a displacement transducer producing displacement pulses, a pulse counting unit, a count comparator unit producing a threshold signal, and a signal delaying unit feeding the threshold signal to a pressure switchover circuit in the pressure control unit.

In a preferred embodiment of the invention, the displacement transducer is carried by the upper press plate, reading the upward displacements of the press table and producing displacement pulses which reflect discrete displacement increments. The operation of the pulse counting unit is controlled by the pressure control unit of the press which sends a count initiation signal, following the receipt of a pressure feedback signal indicating that the contact pressure mode has been established.

The invention further suggests the use of a direction discriminator in conjunction with the pulse counting unit, for the purpose of eliminating from the pulse count any reverse displacement pulses received from the displacement transducer.

The count comparator has a comparison circuit which allows for the adjustment of a threshold value or trigger count, at the attainment of which the comparator produces the threshold signal. The time delay produced by the signal delaying unit is likewise adjustable.

Thus, it is possible to adjust the automatic switchover from the contact pressure mode to the curing pressure mode to the specific requirements of a given bonding layer material and to repeat this switchover accurately during each press cycle, for a consistant multilayer quality. It is no longer necessary to have a device which produces a compression graph during each cycle and a skilled operator which make the switchover decision based on that graph.

BRIEF DESCRIPTION OF THE DRAWING

Further special features and advantages of the invention will become apparent from the description following below, when taken together with the accompanying drawing which illustrates, by way of example, an embodiment of the invention represented in the form of a block diagram showing the components of the device and their interaction.

DESCRIPTION OF THE PREFERRED EMBODIMENT

The drawing shows schematically a heated panel press 10 with a vertically movable lower press plate or press table 11 and a stationary upper press plate 12 engaging and compressing between them a multilayer stack of printed circuit boards 15. A hydraulic press cylinder 13 carries the press table 11, forcing it upwards and thereby creating at least two different pressure modes, while heat is supplied to the multilayer stack 15 via the plates which compress it.

Frequently, the panel press is a multi-stage press having several vertically movable plates in addition to the press table and the stationary top plate, so as to form a number of press gaps, each receiving a multilayer stack. A method and device for producing multilayer printed circuit boards in a duplex multi-stage panel press are disclosed in our copending U.S. patent application, Ser. No. 298,722, filed Sept. 2, 1981.

The level of pressure generated by the hydraulic press cylinder 13 is determined by a pressure control unit 60 and its pressure control connection 62. A pressure feedback connection 63 links a suitable pressure transducing device (not shown) to the pressure control unit 60.

To the panel press 10 and its pressure control unit 60 is connected a flux monitoring and pressure switchover circuit 80, the function of which is to determine the point in time at which the resinous bonding layers in the multilayer stack 15 have reached the flux point and, at a predetermined point later, to signal to the pressure control unit 60 to switch from a contact pressure mode to a curing pressure mode in which a maximum level of pressure is applied to the multilayer stack 15, while the latter cures and hardens.

In order to determine the resin flux point, the panel press has attached to one of its plates 11 or 12 a displacement transducer 20 which produces displacement pulses reflecting increments of vertical movement of the other plate relative to the transducer-carrying plate.

A pulse line 21 transmits the displacement pulses to a pulse counting unit 30. The latter is also connected to the pressure control unit 60 by a counter startup line 61 through which it receives a starting signal for the count, as soon as the pressure control unit 60 receives information from its feedback connection 63 that the contact pressure mode has been established.

With increasing temperature of the multilayer stack 15, its resinous bonding layers soften and the stack height begins to decrease under the action of the contact pressure, as the hydraulic press cylinder 13 and the press table 11 execute small upward displacements. The transducer 20 produces corresponding displacement pulses, transmitting them to a pulse counting unit 30, via the pulse connection 21.

The pulse counting unit 30 adds up all the displacement pulses received during the counting cycle, beginning with the receipt of the count starting signal from the pressure control unit 60. The size of the count is expressed in a correspondingly changing count signal which is transmitted from the counting unit 30 to a comparator unit 40, via the counter exit line 31.

Associated with the counting unit 30 is a direction discriminator 35 which eliminates from the pulse count those displacement pulses which result from an opening movement of the press plate. Such reverse displacements may be produced by the thermal conditions of the press plates themselves.

The comparator unit 40 has stored in it a threshold count $N_F$ which is preadjusted in accordance with an empirically determined height reduction of the multilayer stack under the contact pressure, when the resin of its bonding layers has reached the flux point. As soon as the count signal from the pulse counting unit equals the threshold count, it triggers in the comparator unit a switchover signal which is transmitted to the signal delaying unit 50, via the comparator exit line 32.

The signal delaying unit 50, upon receiving a switchover signal from the comparator unit 40, transmits this signal with a predetermined delay $\Delta t$ to the pressure control unit 60, via the signal connection 33. The amount of delay $\Delta t$ which is applied to the switchover signal is likewise preadjusted in accordance with empirically established data. These data depend, of course, on the specific material characteristics of the bonding layers which are used in the multilayer stacks.

The receipt of the switchover signal by the pressure control unit 60 initiates a change in the pressing action of the panel press 10, the pressure being increased from the comparatively low contact pressure to an elevated curing pressure.

The proposed flux monitoring and pressure switchover circuit 80, consisting of the displacement transducer 20, the pulse counting unit 30 with direction discriminator 35, the comparator unit 40, and the signal delaying unit 50, preferably employ only solid state components in an integrated circuit arrangement, thus making is possible for the switchover control device to take the form of a small accessory unit which is attachable to the heated panel press.

It should be understood, of course, that the foregoing disclosure describes only a preferred embodiment of the invention and that it is intended to cover all changes and modifications of this example of the invention which fall within the scope of the appended claims.

We claim the following:

1. A device for controlling a heated panel press in the switchover from a contact pressure mode to a curing pressure mode, in connection with the assembly of multilayer printed circuit boards with interposed thermosetting resinous bonding layers, the switchover control device comprising in combination:

pressure switchover means operable to change the contact pressure mode of the panel press to the curing pressure mode, in response to the receipt of a threshold signal;

transducer means operable to generate displacement pulses representing increments of displacement between two plates of the panel press through which pressure is applied to a multilayer;

pulse counting means operable to count the displacement pulses received from the transducer means;

count initiating means operable to start the counting means in response to the establishment of the contact pressure mode;

count comparing means operable to produce a threshold signal representing the presence of the flux state of the resin of the bonding layers, when the count of the displacement pulses has reached an empirically predetermined threshold count; and signal delaying means operable to transmit the threshold signal to the pressure switchover means with an adjustable time delay.

2. A switchover control device as defined in claim 1, further comprising pulse discriminating means associated with the pulse counting means and operable to block transmission to the pulse counting means of all pulses other than those which are indicative of press plate approaching displacements.

3. A switchover control device as defined in claim 1 or claim 2, wherein the device is adapted for use with a hydraulically driven panel press which includes a pressure control unit;

the pressure switchover means forms a part of the pressure control unit; and the count initiating means includes a hydraulic pressure feedback, as part of the pressure control unit.

4. A switchover control device as defined in claim 3, wherein the pulse counting means, the pulse discriminating means, the count comparison means, and the signal delaying means are parts of an integrated switchover circuit.

* * * * *